US00PP18078P2

(12) United States Plant Patent
Oostveen

(10) Patent No.: US PP18,078 P2
(45) Date of Patent: Sep. 25, 2007

(54) *ABUTILON* PLANT NAMED 'OOSTTRUMP'

(50) Latin Name: ***Abutilon* hybrid**
Varietal Denomination: Oosttrump

(75) Inventor: Wijnand Oostveen, De Kwakel (NL)

(73) Assignee: De Zonnebloem Jouge Planten BV, De Kwakel (NL)

( * ) Notice: Subject to any disclaimer, the term of this patent is extended or adjusted under 35 U.S.C. 154(b) by 0 days.

(21) Appl. No.: 11/311,673

(22) Filed: Dec. 19, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

Upov–Rom Plant Variety Database 2006/03 for cultivar OOSTTRUM.*

* cited by examiner

*Primary Examiner*—Kent Bell
*Assistant Examiner*—Annette H Para
(74) *Attorney, Agent, or Firm*—C. A. Whealy

(57) ABSTRACT

A new and distinct cultivar of *Abutilon* plant named 'Oosttrump', characterized by its compact, upright to outwardly spreading and weeping plant habit; freely branching habit; dark green-colored leaves; freely flowering habit; and pale yellow-colored flowers.

1 Drawing Sheet

Botanical designation: *Abutilon* hybrid.
Cultivar denomination: 'Oosttrump'.

BACKGROUND OF THE INVENTION

The present Invention relates to a new and distinct cultivar of *Abutilon* plant, botanically known as *Abutilon* hybrid, and hereinafter referred to by the name 'Oosttrump'.

The new cultivar is a product of a planned breeding program conducted by the Inventor in Venlo, The Netherlands. The objective of the breeding program was to develop new compact *Abutilon* cultivars with attractive flower coloration.

The new cultivar originated from a cross-pollination made by the Inventor during the summer of 2003 of the *Abutilon megabotanicum* cultivar Kentisch, not patented, as the female, or seed, parent with an unnamed selection of *Abutilon* hybrid, not patented, as the male, or pollen, parent. The new cultivar was discovered and selected by the Inventor as a flowering plant within the progeny from this cross-pollination in a controlled environment in Venlo, The Netherlands during the spring of 2004.

Asexual reproduction of the new cultivar by terminal cuttings in De Kwakel, The Netherlands since October, 2004, has shown that the unique features of this new *Abutilon* are stable and reproduced true to type in successive generations.

SUMMARY OF THE INVENTION

Plants of the cultivar Oosttrump have not been observed under all possible environmental conditions. The phenotype may vary somewhat with variations in environment such as temperature and light intensity without, however, any variance in genotype.

The following traits have been repeatedly observed and are determined to be the unique characteristics of 'Oosttrump'. These characteristics in combination distinguish 'Oosttrump' as a new and distinct cultivar:

1. Compact, upright to outwardly spreading and weeping plant habit.
2. Freely branching habit.
3. Dark green-colored leaves.
4. Freely flowering habit.
5. Pale yellow-colored flowers.

Plants of the new *Abutilon* can be compared to plants of the female parent, the cultivar Kentisch. In side-by-side comparisons conducted in Venlo, The Netherlands, plants of the new *Abutilon* differed from plants of the cultivar Kentisch in the following characteristics:

1. Plants of the new *Abutilon* were more freely branching than plants of the cultivar Kentisch.
2. Plants of the new *Abutilon* and the cultivar Kentisch differed in flower color as plants of the cultivar Kentisch had yellow and brown-colored flowers.

Plants of the new *Abutilon* can be compared to plants of the male parent selection. In side-by-side comparisons conducted in Venlo, The Netherlands, plants of the new *Abutilon* differed from plants of the male parent selection in the following characteristics:

1. Plants of the new *Abutilon* were more freely branching than plants of the male parent selection.
2. Plants of the new *Abutilon* had smaller and more campanulate flowers than plants of the male parent selection.

Plants of the new *Abutilon* can be compared to plants of the *Abutilon* cultivar, 'Julia', not patented. In side-by-side comparisons conducted in Venlo, The Netherlands, plants of the new *Abutilon* differed from plants of the cultivar Julia in the following characteristics:

1. Plants of the new *Abutilon* were more freely branching than plants of the cultivar Julia.
2. Plants of the new *Abutilon* had smaller leaves than plants of the cultivar Julia.
3. Plants of the new *Abutilon* had smaller and more campanulate flowers than plants of the cultivar Julia.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Abutilon*.

The photograph at the top of the sheet comprises a side perspective view of a typical flowering plant of 'Oosttrump'.

The photograph at the middle of the sheet is a close-up view of the upper surfaces of typical leaves and flowers of 'Oosttrump'.

The photograph at the bottom of the sheet is a close-up view of the lower surfaces of typical leaves and flowers of 'Oosttrump'.

DETAILED BOTANICAL DESCRIPTION

In the following description, color references are made to The Royal Horticultural Society Colour Chart, 2001 Edition, except where general terms of ordinary dictionary significance are used.

Plants used for the aformentioned photographs and following description were about one year old and grown in 10.5-cm containers in a glass-covered greenhouse during the summer in De Kwakel, The Netherlands. During the production of the plants, day temperatures ranged from 18° C. to 27° C. and night temperatures ranged from 12° C. to 22° C. Plants were pinched one time about six to seven weeks after planting.

Botanical classification: *Abutilon* hybrid cultivar Oosttrump.

Parentage:

*Female, or seed, parent.*—*Abutilon megabotanicum* cultivar Kentisch, not patented.

*Male, or pollen, parent.*—Unnamed selection of *Abutilon* hybrid, not patented.

Propagation:

*Type.*—Terminal cuttings.

*Time to initiate roots, summer.*—About 14 days at 22° C.

*Time to initiate roots, winter.*—About 18 days at 18° C.

*Time to develop roots, summer.*—About four weeks at 22° C.

*Time to develop roots, winter.*—About five weeks at 18° C.

*Root description.*—Fine; slightly fleshy; creamy white in color.

*Rooting habit.*—Freely branching; dense.

Plant description:

*Form.*—Compact, upright and outwardly spreading to weeping plant habit. Freely branching habit, about six lateral branches per plant. Low to moderate vigorous growth habit.

*Plant height.*—About 24 cm.

*Plant diameter.*—About 27.5 cm.

*Lateral branches.*—Length: About 12.5 cm. Diameter: About 3 mm. Internode length: About 1.7 cm. Shape: Round in cross-section. Strength: Strong. Texture: Smooth, glabrous. Color, developing stems: 143A. Color, mature stems: 147A.

*Foliage description.*—Arrangement: Alternate; simple. Length: About 7.8 cm. Width: About 5.4 cm. Shape: Ovate; palmately lobed. Apex: Acute. Base: Hastate. Margin: Palmately lobed; serrate. Texture, upper and lower surfaces: Smooth, glabrous. Venation pattern: Palmate; lacinate. Petiole length: About 3.7 cm. Petiole diameter: About 1 mm. Petiole texture, upper and lower surfaces: Smooth, glabrous. Color: Developing foliage, upper surface: 143B. Developing foliage, lower surface: 143C. Fully expanded foliage, upper surface: In between 137A and 139A; venation, 137A. Fully expanded foliage, lower surface: 137C; venation, 138B. Petiole, upper surface: 143A. Petiole, lower surface: 143B to 143C.

Flower description:

*Flower type and habit.*—Single campanulate flowers; flowers drooping. Flowers not persistent. Freely flowering, about seven open flowers and flower buds per lateral branch.

*Natural flowering season.*—May into October in The Netherlands; flowering continuous during this period.

*Flower longevity on the plant.*—About one week.

*Fragrance.*—None detected.

*Flowers.*—Appearance: Flared campanulate, corolla with five separate petals; flowers rotate. Diameter: About 4.1 cm. Depth (length): About 3.2 cm.

*Flower buds.*—Length: About 2.2 cm. Diameter: About 1.1 cm. Shape: Ovate. Color: 150B to 150C; towards the base, 143C; towards the apex, 6C.

*Petals.*—Arrangement: Single whorl of five separate petals. Length: About 3.4 cm. Width: About 1.7 cm. Shape: Oblanceolate. Apex: Broadly acute to obtuse. Base: Attenuate. Margin: Entire. Texture, upper and lower surfaces: Smooth, glabrous; satiny. Color: When opening, upper and lower surfaces: 6C; towards the base, 3C. Fully opened, upper and lower surfaces: 6C; towards the base, 3C.

*Sepals.*—Arrangement: Five per flower in a single whorl; campanulate calyx. Length: About 2.2 mm. Width: About 7 mm. Shape: Narrowly ovate. Apex: Acute. Base: Broadly cuneate, fused. Margin: Entire. Texture, upper surfaces: Densely pubescent. Texture, lower surface: Smooth, glabrous. Color, immature, upper and lower surfaces: 150B to 150C; towards the base, 143C. Color, mature, upper and lower surfaces: 145A to 145B; towards the base, 143C.

*Peduncles.*—Length: About 3.4 cm. Diameter: About 1 mm. Angle: About 30° from vertical. Strength: Strong. Texture: Smooth, glabrous. Color: 143A.

*Reproductive organs.*—Stamens: Quantity/arrangement: About 100; filaments fused into a tube; anthers, dorsifixed. Anther shape: Orbicular. Anther size: About 3 mm by 0.5 mm. Anther color: 12A to 12B. Filament color: 11A. Pollen amount: Abundant. Pollen color: 13A. Pistils: Quantity: Typically six. Pistil length: About 4 mm. Stigma shape: Terete. Stigma color: 11D. Style length: About 3 mm. Style color: 1C. Ovary color: 150B.

*Fruits.*—Quantity per plant: About six. Length: About 1.3 cm. Diameter: About 1.5 cm. Texture: Densely pubescent. Color: 145A to 145B.

*Seeds.*—Quantity per fruit: About 16. Length: About 3 mm. Diameter: About 2 mm. Color: Close to 155A.

Disease/pest resistance: Plants of the new *Abutilon* have not been noted to be resistant to pathogens and pests common to *Abutilon*.

Temperature tolerance: Plants of the new *Abutilon* have been observed to be tolerant to rain and wind and tolerant to temperatures from about 0° C. to about 35° C.

It is claimed:

1. A new and distinct cultivar of *Abutilon* plant named 'Oosttrump', as illustrated and described.

* * * * *

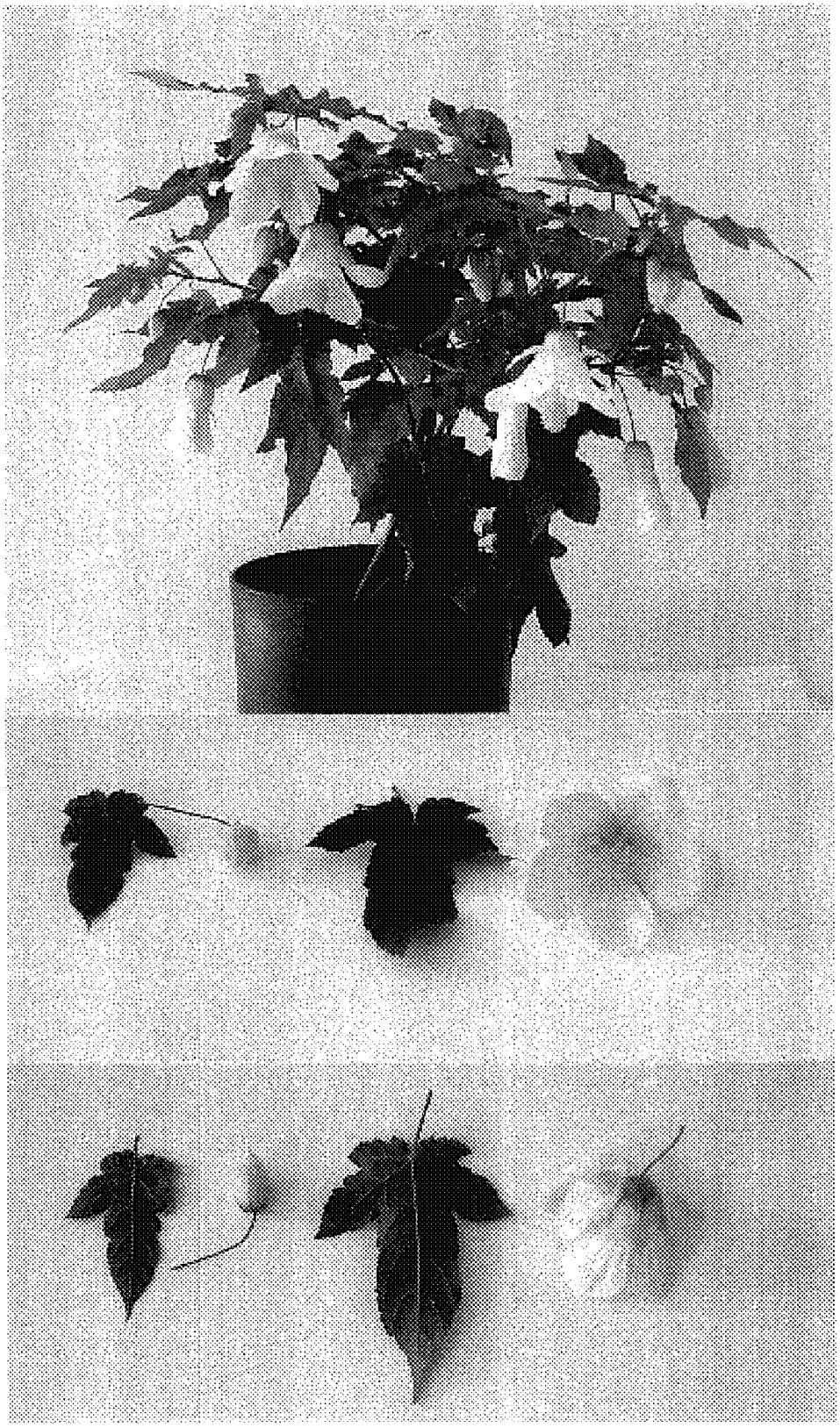

UNITED STATES PATENT AND TRADEMARK OFFICE

CERTIFICATE OF CORRECTION

PATENT NO. : PP 18,078 P2
APPLICATION NO. : 11/311673
DATED : September 25, 2007
INVENTOR(S) : Wijnand Oostveen It is certified that error appears in the above-identified patent and that said Letters Patent is hereby corrected as shown below:

On the title page, item [73] should read:

Assignee: De Zonnebloem [Jonge Planten BV.] B.V.

Signed and Sealed this

Twenty-fourth Day of February, 2009

JOHN DOLL
*Acting Director of the United States Patent and Trademark Office*